United States Patent [19]
Collins et al.

[11] 4,182,727
[45] Jan. 8, 1980

[54] 4-[6-(4-CYANOPHENOXY)HEXYL]-3,5-HEPTANEDIONE

[75] Inventors: Joseph C. Collins, East Greenbush; Guy D. Diana, Stephentown, both of N.Y.

[73] Assignee: Sterling Drug Inc., New York, N.Y.

[21] Appl. No.: 913,366

[22] Filed: Jun. 7, 1978

Related U.S. Application Data

[60] Division of Ser. No. 725,160, Sep. 21, 1976, Pat. No. 4,133,959, which is a continuation-in-part of Ser. No. 576,311, May 12, 1975, Pat. No. 4,031,246, which is a continuation-in-part of Ser. No. 381,406, Jul. 23, 1973, Pat. No. 3,933,837.

[51] Int. Cl.$^2$ ............................................. C07C 121/75

[52] U.S. Cl. .................................. 260/465 F; 260/511; 260/556 AR; 260/593 R; 560/174; 424/315; 424/321; 568/610

[58] Field of Search ...................................... 260/465 F

[56] References Cited
U.S. PATENT DOCUMENTS 3,541,155  11/1970  D'Amico ............................. 260/590

*Primary Examiner*—Dolph H. Torrence
*Attorney, Agent, or Firm*—Thomas L. Johnson; B. Woodrow Wyatt

[57] ABSTRACT

Sulfo- and aminosulfonyl-substituted aryloxyalkyl diketones, useful as anti-viral agents, are prepared, respectively, by reacting a phenoxyalkyl diketone with sulfuric acid; or by reacting a haloalkyl diketone with an alkali metal salt of a hydroxybenzenesulfonamide.

1 Claim, No Drawings

4-[6-(4-CYANOPHENOXY)HEXYL]-3,5-HEPTANEDIONE

This application is a divisional of copending application Ser. No. 725,160, filed Sept. 21, 1976, now U.S. Pat. No. 4,133,959 which is in turn a continuation-in-part of copending application Ser. No. 576,311, filed May 12, 1975, now U.S. Pat. No. 4,031,246, which is in turn a continuation-in-part of application Ser. No. 381,406, filed July 23, 1973, now U.S. Pat. No. 3,933,837.

BACKGROUND OF THE INVENTION (a) Field of the Invention

This invention relates to aryloxyalkyl diketone and keto-esters, to the preparation thereof and to compositions and methods for the use thereof as anti-viral agents.

(b) Description of the Prior Art

Chodnekar et al. U.S. Pat. No. 3,686,222 discloses ethers of the formula R—O—Ar wherein Ar is methylenedioxyphenyl and R is an aliphatic hydrocarbon radical or an epoxide derivative thereof. useful as pesticides having juvenile hormone activity, Erickson U.S. Pat. No. 3,787,443 discloses ethers of the formula R—O—Ar wherein Ar is methylenedioxyphenyl or other substituted phenyl groups, and R is an aliphatic hydrocarbon radical or an epoxide or episulfide derivative thereof, useful as pesticides having juvenile hormone activity.

Collins U.S. Pat. No. 3,829,475 discloses diketones and keto-esters of the formula RR'CH—Alk—Ar wherein R is acyl, R' is acyl or carboalkoxy, Alk is an alkylene bridge and Ar is phenyl or substituted phenyl, useful as pesticidal and anti-viral agents; no aryl ethers are disclosed.

SUMMARY OF THE INVENTION

In a composition of matter aspect, the invention relates to compounds of the formula RR'CH—Alk—O—Ar wherein R is alkanoyl or carbalkoxy, R' is alkanoyl, Alk is alkylene and Ar is phenyl or substituted phenyl, useful as anti-viral agents.

In further composition of matter aspects, the invention relates to intermediates of the formula RR'CH—Alk—X where Alk is alkylene and X is Br and I; and intermediates of the formula 2-Cl-4-CH₃O—C₆H₃—O—Alk'—Cl where Alk' is alkylene interrupted by an oxygen atom.

In a further composition of matter aspect, the invention relates to a composition for combatting viruses which comprises an antivirally effective amount of a compound of the formula RR'CH—Alk—O—Ar in admixture with a suitable carrier or diluent.

In a process aspect, the invention relates to a process for obtaining the compounds of the invention by treating a compound of the formula X—Alk—O—Ar, where X is bromine or iodine, with a compound of the formula RR'CH⁻M⁺ where M⁺ is an alkali metal cation; or, conversely, reacting a compound of the formula RR'CH—Alk—X with a compound of the formula ArO⁻M⁺.

In a further process aspect, the invention relates to a method for combatting viruses which comprises contacting the locus of said viruses with an anti-virally effective amount of a compound of the formula RR'CH—Alk—OAr in admixture with a suitable carrier or diluent.

DETAILED DESCRIPTION INCLUSIVE OF PREFERRED EMBODIMENTS

The compounds of the invention are of the structural formula

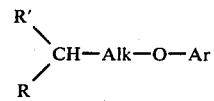

wherein:

Alk is alkylene of 3 to 10 carbon atoms optionally interrupted by an oxygen atom separated by at least two carbon atoms from the terminal bonds of Alk;

R is alkanoyl of 2 to 6 carbon atoms;

R' is alkanoyl of 2 to 6 carbon atoms or carboalkoxy of 2 to 6 carbon atoms;

and Ar is phenyl or phenyl substituted by one to three substituents selected from the group consisting of alkyl of 1 to 4 carbon atoms, alkoxy of 1 to 4 carbon atoms, alkylthio of 1 to 4 carbon atoms, alkoxyalkoxy of 3 to 6 carbon atoms, hydroxyalkoxy of 2 to 4 carbon atoms, halogen, cyano, nitro, acetyl, sulfo, aminosulfonyl, trifluoromethyl, trifluoromethoxy, hydroxy, benzyloxy, carboxy, carboalkoxy of 2 to 4 carbon atoms, acyloxy of 1 to 10 carbon atoms, dialkylamino where alkyl has from 1 to 4 carbon atoms, and dialkylaminoalkoxy where alkyl has from 1 to 4 carbon atoms and alkoxy has from 2 to 4 carbon atoms.

Also within the scope of the invention are pharmaceutically acceptable heavy metal chelates of the foregoing compounds, wherein the metal is complexed with the carbonyl groups of the diketone or keto-ester moiety. Such metals include copper (valence II), nickel, cobalt and the like.

In the above general formula I, Alk stands for a saturated aliphatic hydrocarbon bridge containing from 3 to 10 carbon atoms. The alkylene bridge may be straight or branched. A preferred class of compounds are those where Alk is straight chain alkylene of 3 to 10 carbon atoms, and if the Alk bridge is branched, it is preferred that it be symmetrical, that is with the branching at the same relative positions from either end of the bridge.

The alkylene bridge, Alk, is optionally interrupted by an oxygen atom separated by at least two carbon atoms from the terminal bonds of Alk. The oxygen atom is preferably in the center of the alkylene bridge, equidistant from the terminal bonds of Alk.

The carbon chains of R and R' can be straight or branched.

When two or three monovalent substituents are present on the phenyl ring of Ar, they can be the same or different. In the event alkoxyalkoxy is present on the phenyl ring, it is preferred that the two oxygen atoms therein be separated by at least two carbon atoms. It is also preferred that no more than one nitro or sulfo group be present on the phenyl ring.

The compounds of the invention are prepared according to the following reaction sequence:

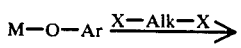 

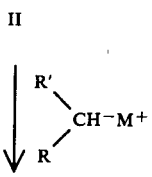

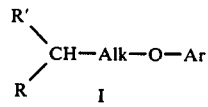

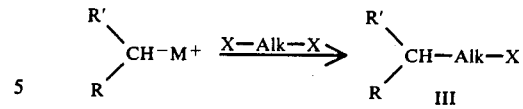

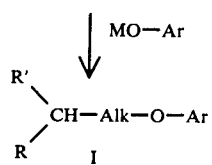

An alkali metal salt of a phenol (HOAr), M—O—Ar, where M is alkali metal, preferably sodium or potassium, is interacted with an alkylene dihalide, X—Alk—X, where X is chlorine, bromine or iodine. The reaction takes place with moderate heating, between about 50° and 100° C. in an inert solvent using equimolar quantities of reactants, or preferably a stoichiometric excess of dihalide to minimize di-ether (Ar—O—Alk—O—Ar) formation. The di-ether that is formed is readily separated from the desired mono-ether (II), because the former is a relatively high melting solid which separates readily from organic solvents while the mono-ether remains in solution.

In the final step, the mono-ether, X—Alk—O—Ar (II), is treated with the alkali metal enolate salt of a diketone or keto-ester of formula RR'CH$^-$M$^+$, where R and R' have the meanings given hereinabove and M$^+$ is an alkali metal cation, preferably lithium, sodium or potassium. The reaction takes place in an inert solvent under anhydrous conditions at ambient temperature or slightly above (25°–70° C.). If the mono-ether, X—Alk—O—Ar, is a chloride (X=Cl), it is preferably converted to the more reactive iodide (X=I) with an alkali metal iodide, prior to the final alkylation step.

If it is desired to obtain compounds of formula I wherein Ar is substituted by one to three hydroxy groups, the reaction between M—OAr and X—Alk—X can be carried out with the corresponding compounds where Ar is substituted by one to three benzyloxy or acyloxy groups. The benzyloxy or acyloxy group or groups can then be cleaved by catalytic hydrogenolysis or hydrolysis, respectively.

It is not, however, essential that phenolic hydroxy groups be protected in the form of ethers or esters at the final stage of the synthesis because the diketone or keto-ester reactant, RR'CH$_2$, is more acidic than the phenolic hydroxyl; hence the desired alkylation with the iodides or bromides (II, X is I or Br) will take place without affecting any phenolic hydroxy groups which may be present.

Alternatively, in the final step, the alkali metal enolate salt can be replaced by a heavy metal chelate of the diketone or keto-ester. Appropriate heavy metal chelates include the copper, nickel and cobalt chelates.

An alternative approach to the compounds of the invention is depicted in the following reaction sequence:

In this alternative approach an alkali metal enolate salt or a heavy metal chelate of a diketone or keto-ester (RR'CH$_2$) is interacted with an alkylene dihalide, X—Alk—X. The reaction takes place in an inert solvent under anhydrous conditions at ambient temperature or slightly above (20°–70° C.), using equimolar quantities of reactants or a stoichiometric excess of dihalide. The resulting haloalkyl diketone or keto-ester of formula III is then interacted with an alkali metal salt of a phenol (HOAr), which reaction takes place with moderate heating, between about 50° and 100° C. in an inert solvent under anhydrous conditions. In this approach, any free hydroxy groups present in Ar should be protected in the form of the benzyl ether or an ester in order to prevent competing reactions with the haloalkyl diketone.

The intermediates of formula III are novel compounds and within the purview of the invention.

It is preferred to carry out the initial etherification step with a dibromide (X—Alk—X where X is Br) because of the more ready availability of dibromides as compared to diiodides. The resulting bromide (X—Alk—O—Ar or RR'CH—Alk—X where X is Br) can be interacted directly with the alkali metal enolate salt RR'CH$^-$M$^+$ or phenolate ArO$^-$M$^+$, respectively; or if desired converted to the corresponding iodide (X—Alk—O—Ar or RR'CH—Alk—X where X is I) which reacts somewhat more easily with the enolate or phenolate salt than does the bromide. The conversion of II (X=Br) to II (X=I) or III (X=Br) to III (X=I) is effected by heating the former with sodium or potassium iodide in an inert solvent, e.g. acetone.

The dihalides, X—Alk—X, where Alk is branched or oxygen interrupted are preferably symmetrical, that is, the branching or hetero atom is in the same relative position or positions with respect to the terminal halogen atoms, in order to avoid production of mixtures upon ether formation.

It is also possible to employ chlorobromoalkanes as the dihalide reactant, namely, Cl—Alk—Br. The use of such mixed dihalides has the advantage that di-ether formation is eliminated or minimized, since reaction occurs preferentially with the bromine atom, especially if stoichiometric proportions of phenol and dihalide are used. Furthermore, it is possible by this variation in the procedure to obtain compounds with unsymmetrically branched or oxygen interrupted alkylene bridges without producing mixtures. The resulting chloroalkoxy aryl ether, Cl—Alk—O—Ar, or chloroalkyl diketone or keto-ester, Cl—Alk—CHR'R, must then be converted to the corresponding bromo or iodo compound before it will react with the alkali metal phenolate or the alkali metal enolate salt of a diketone or keto-ester, respectively. The chlorobromoalkane starting materials can be prepared by reduction, e.g. with lithium aluminum hydride, of a chloro-ester, Cl—Alk'—COOCH$_3$, to afford a chloroalkanol, Cl—Alk—OH, followed by replacement of the hydroxy group with bromine, e.g. with phosphorus tribromide.

It is preferred to prepare compounds of formula I where the aryl group is substituted by acyloxy by esterification of the corresponding hydroxy compounds with the appropriate acid halide or acid anhydride. The acyloxy groups are derived from carboxylic acids having from one to about ten carbon atoms, and having a molecular weight less than about 200. Representative of the acyl radicals which can be present are lower-alkanoyl radicals, e.g., formyl, acetyl, propionyl, butyryl, isobutyryl, caproyl, heptanoyl, octanoyl, trimethylacetyl, and the like; carboxy-lower-alkanoyl radicals, e.g., succinyl (β-carboxypropionyl); cycloalkyl-lower-alkanoyl radicals, e.g., β-cyclopentylpropionyl, β-cyclohexylpropionyl, and the like; monocarbocyclic aroyl radicals, e.g., benzoyl, p-toluyl, p-nitrobenzoyl, 3,4,5-trimethoxybenzoyl, and the like; monocarbocyclic aryl-lower-alkanoyl or -alkenoyl radicals, such as phenylacetyl, β-phenylpropionyl, cinnamoyl, and the like; and monocarbocyclic aryloxy-lower-alkanoyl radicals, such as p-chlorophenoxyacetyl, and the like; and amino-lower-alkanoyl, such as glycinyl, alaninyl, diethylaminopropionyl, piperidinopropionyl, pyrrolidinopropionyl, morpholinobutyryl, and the like. When monocarbocyclic aryl groups are present in the ester moieties, monocarbocyclic aryl includes phenyl and phenyl substituted by from one to three lower-alkyl, lower-alkoxy, halogen or nitro groups, which substituents, if plural, can be the same or different. It is preferred that no more than one nitro group be present.

It is preferred to prepare compounds of formula I where the aryl group is substituted by carboxyl (COOH) by hydrolysis of the corresponding compounds of formula I where the aryl group is substituted by carboalkoxy. A sulfo group can be introduced into the aryl group of a compound of formula I by direct sulfonation with sulfuric acid.

It is preferred to prepare compounds of formula I where the aryl group is substituted by dialkylaminoalkoxy by etherification of the corresponding compounds of formula I where the aryl group is substituted by hydroxy, effected by reacting an alkali metal salt of the latter with a dialkylaminoalkyl halide.

Biological evaluation of the compounds of the invention has shown that they possess antiviral activity. They have been found to be effective against one or more of a large variety of RNA and DNA viruses, including Myxoviruses, e.g. influenza types A$_0$, A$_1$, A-2, B; Paramyxoviruses, e.g. parainfluenza types 1, 2, 3, and mumps virus; Picornaviruses, e.g. human rhinoviruses, Coxsackie viruses types A, B, ECHO viruses, equine rhinoviruses; Reoviruses, types 1, 2, 3; Arboviruses, e.g. equine encephalomyelitis (Eastern, Western and Venezuelan), Semliki Forest virus; miscellaneous RNA viruses, e.g. measles, distemper, respiratory syncytial, rubella, vesicular stomatitis, hepatitis; Herpes viruses, e.g. HSV type I, II, herpesvirus simiae, herpes-virus varicellae, infectious bovine rhinotracheitis, cytomegalovirus, Marek's disease virus, Epstein-Barr virus; Poxviruses, e.g. variola, vaccinia; leukemogenic viruses. Both in vitro and in vivo antiviral activity have been found in the compounds of the invention. The in vitro testing of the compounds showed that they had minimal growth inhibitory concentrations (mic) ranging from about 0.3 to about 50 micrograms per milliliter. The mic values were determined by standard serial dilution procedures.

The structures of the compounds of the invention were established by the modes of synthesis, by elementary analysis, and by infrared and nuclear magnetic resonance spectral determinations.

A still further aspect of the invention relates to compositions for combatting viruses which comprise an antivirally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

EXAMPLE 1

(a) 4-(6-Bromohexyl)-3,5-heptanedione

A solution of 64.1 g. of 3,5-heptanedione in 200 ml. of dimethylformamide was added over a period of one hour to a suspension of 3.65 g. of lithium hydride in 400 ml. of dimethylformadie. The mixture was stirred for one hour and 488 g. of 1,6-dibromohexane was then added all at once. The reaction mixture was warmed at 60°–70° C. for 24 hours. The volatile solvent was removed and the residue partitioned between water and methylene dichloride. The methylene dichloride solution was concentrated and the residue distilled to give 65.0 g. of 4-(6-bromohexyl)-3,5-heptanedione, b.p. 118°–124° C. (0.005 mm.).

By substituting for the 1,6-dibromohexane the corresponding homologous dibromoalkanes, there were prepared 4-(8-bromooctyl)-3,5-heptanedione, b.p. 136°–139° C. (0.004 mm.); 4-(9-bromononyl)-3,5-heptanedione, b.p. 135°–137° C. (0.004 mm.); and 4-(10-bromodecyl)-3,5-heptanedione, b.p. 157°–159° C. (0.005 mm.).

By selecting the appropriate alkane dibromide and dione, there can be prepared 3-(3-bromopropyl)-2,4-pentanedione, 4-(6-bromohexyl)-2,2,6,6-tetramethyl-3,5-pentanedione, 5-(6-bromohexyl)-4,6-nonanedione, and the like.

(b) 4-[6-(4-Aminosulfonylphenoxy)hexyl]-3,5-heptanedione [I; Ar is 4-H$_2$NSO$_2$C$_6$H$_4$, Alk is (CH$_2$)$_6$, R and R' are CH$_3$CH$_2$CO]

A mixture of 18.2 g. of 4-hydroxybenzenesulfonamide, 33.6 g. of 4-(6-bromohexyl)-3,5-heptanedione, 18.3 g. of powdered anhydrous potassium carbonate and 175 ml. of acetone was stirred at reflux for 24 hours. The reaction mixture was cooled, filtered to remove salts, and concentrated in vacuo. The solid residue was recrystallized from an acetone--ether mixture to give 4-[6-(4-aminoslufonylphenoxy)hexyl]-3,5-heptanedione, m.p. 86°–87° C. (light yellow solid).

Anal. Calcd. for $C_{19}H_{29}NO_5S$: C, 59.51; H, 7.62; N, 3.65; S, 8.36. Found: C, 59.18; H, 7.61; N, 3.67; S, 8.37.

By substituting for the 4-(6-bromohexyl)-3,5-heptanedione in the foregoing example a molar equivalent amount of 3-(3-bromopropyl)-2,4-pentanedione, 4-(10-bromodecyl)-3,5-heptanedione or 5-(6-bromohexyl)-4,6-nonanedione, there can be obtained, respectively, 3-[3-(4-aminosulfonylphenoxy)propyl]-2,4-pentanedione [I; Ar is 4-$H_2NSO_2C_6H_4$, Alk is $(CH_2)_3$, R and R' are $CH_3CO$]; 4-[10-(4-aminosulfonylphenoxy)decyl]-3,5-heptanedione ]I; Ar is $H_2NSO_2C_6H_4$, Alk is $(CH_2)_{10}$, R and R' are $CH_3CH_2CO$]; or 5-[6-(4-aminosulfonylphenoxy)hexyl]-4,6-nonanedione [I; Ar is 4-$H_2NSO_2C_6H_4$, Alk is $(CH_2)_6$, R and R' are $CH_3CH_2CH_2CO$].

EXAMPLE 2

4-[6-(4-Sulfophenoxy)hexyl]-3,5-heptanedione [I; Ar is 4-$HO_3SC_6H_4$, Alk is $(CH_2)_6$, R and R' are $CH_3CH_2CO$].

A mixture of 10.2 g. of 4-(6-phenoxyhexyl)-3,5-heptanedione (prepared from 6-phenyloxyhexyl bromide and lithium 3,5-heptanedione) and 2.13 ml. of concentrated sulfuric acid was heated on a steam bath for one hour. The reaction mixture was cooled, ice added, and the solution neutralized with aqueous potassium hydroxide. The solid product which formed was collected by filtration, washed with cold water and recrystallized from water to give 5.6 g. of 4-[6-(4-sulfophenoxy)hexyl]-3,5-heptanedione in the form of its potassium salt, m.p. 260° C.

Anal. Calcd. for $C_{19}H_{27}KO_6S$: C, 53.09; H, 6.51; S, 7.25. Found: C, 52.90; H, 6.53; S, 7.22.

EXAMPLE 3

(a) 2-[2-(2-Chloro-4-methoxyphenoxy)ethoxy]ethyl chloride

To a suspension of 9.6 g. of 50% sodium hydride in 250 ml. of dry dimethylformamide was added in portions 31.6 g. of 2-chloro-4-methoxyphenol. To this mixture was added 143 g. of bis(2-chloroethyl) ether, and the reaction mixture was heated at reflux with stirring for eight hours. The volatile solvent was removed, the residue partitioned between water and methylene dichloride, and the organic solution washed with water and dried over anhydrous magnesium sulfate. The product was twice distilled to give 2-[2-(2-chloro-4-methoxyphenoxy)ethoxy]ethyl chloride, b.p. 139°–140° C. (0.05 mm.).

Anal. Calcd. for $C_{11}H_{14}Cl_2O_3$: C, 60.11; H, 7.06; Cl, 8.87. Found: C, 60.20; H, 7.15; Cl, 9.25.

Similarly, by replacing the bis(2-chloroethyl) ether with bis(4-chlorobutyl) ether, there was obtained 4-[4-(2-chloro-4-methoxyphenoxy)butoxy]butyl chloride, b.p. 165°–170° C. (0.1 mm.).

Anal. Calcd. for $C_{15}H_{22}Cl_2O_3$: C, 56.08; H, 6.90; Cl, 22.07.

Found: C, 56.13; H, 7.01; Cl, 21.78.

(b) 2-[2-(2-Chloro-4-methoxyphenoxy)ethoxy]ethyl iodine was prepared from 24.7 g. of the corresponding chloride of part (a) by three hours reflux with 13.5 g. of sodium iodide in 200 ml. of 2-butanone. The crude product was used directly in part (c) below.

(c)

4-{2-[2-(2-Chloro-4-methoxyphenoxy)ethoxy]ethyl}-3,5-heptanedione [I; Ar is 2-Cl-4-$CH_3OC_6H_3$, Alk is $(CH_2)_2O(CH_2)_2$, R and R' are $CH_3CH_2CO$]

was prepared from 65.1 g. of the iodide from part (b) and the lithium salt derived from 41.0 g. of 3,5-heptanedione to give 12.1 g. of product, b.p. 168°–172° C. (0.005 mm.).

Anal. Calcd. for $C_{18}H_{24}ClO_5$: C, 60.59; H, 7.06; Cl, 9.94. Found: C, 60.35; H, 7.24; Cl, 9.85.

Similarly, 4-[4-(2-chloro-4-methoxyphenoxy)butoxy]butyl chloride was converted to 4-{4-[4-(2-chloro-4-methoxyphenoxy)butoxy]butyl}-3,5-heptanedione [I; Ar is 2-Cl-4-$CH_3OC_6H_3$, Alk is $(CH_2)_4O(CH_2)_4$, R and R' are $CH_3CH_2CO$].

EXAMPLE 4

4-[6-(4-Cyanophenoxy)hexyl]-3,5-heptanedione [I; Ar is 4-$NCC_6H_4$, Alk is $(CH_2)_6$, R and R' are $CH_3CH_2CO$]

Sodium hydride (2.04 g., 0.042 mole, dispersion in oil) was washed free of oil with n-hexane and suspended in 75 ml. of dry dimethylformamide. To this suspension was added slowly 5.0 g. (0.042 mole) of 4-cyanophenol followed by 11.7 g. (0.04 mole) of 4-(6-bromohexyl)-3,5-heptanedione. The reaction mixture was stirred on a steam bath for three hours and then poured onto ice and dilute hydrochloric acid. The mixture was extracted with methylene dichloride, washed with water, dried over anhydrous magnesium sulfate and concentrated. The residue was distilled twice to afford 4.4 g. of 4-[6-(4-cyanophenoxy)hexyl]-3,5-heptanedione, b.p. 205°–210° C. (0.005 mm.).

Anal. Calcd. for $C_{20}H_{27}NO_3$: C, 72.92; H, 8.26; N, 4.25. Found: C, 73.15; H, 8.35; N, 4.28.

We claim:

1. 4-[6-(4-Cyanophenoxy)hexyl]-3,5-heptanedione.

* * * * *

UNITED STATES PATENT AND TRADEMARK OFFICE
CERTIFICATE OF CORRECTION

PATENT NO. : 4,182,727

DATED : January 8, 1980

INVENTOR(S) : Joseph C. Collins and Guy D. Diana

It is certified that error appears in the above-identified patent and that said Letters Patent are hereby corrected as shown below:

Column 6, line 35, "dimethylformadie" should read --dimethylformamide--.

Column 7, line 1, "aminoslufonylphenoxy" should read --aminosulfonylphenoxy--.

Column 8, line 12, "iodine" should read --iodide--; line 26, "$C_{18}H_{24}ClO_5$" should read --$C_{18}H_{25}ClO_5$--.

Signed and Sealed this

Twentieth Day of May 1980

[SEAL]

Attest:

SIDNEY A. DIAMOND

Attesting Officer

Commissioner of Patents and Trademarks